US008475375B2

(12) United States Patent
Smith et al.

(10) Patent No.: US 8,475,375 B2
(45) Date of Patent: Jul. 2, 2013

(54) SYSTEM AND METHOD FOR ACTIVELY COOLING AN ULTRASOUND PROBE

(75) Inventors: Lowell Scott Smith, Niskayuna, NY (US); Robert Stephen Lewandowski, Amsterdam, NY (US); Bruno Hans Haider, Ballston Lake, NY (US); Charles Edward Baumgartner, Schenectady, NY (US); George Charles Sogoian, Glenville, NY (US); Christopher Stephen Yetter, Scotia, NY (US); Douglas Glenn Wildes, Ballston Lake, NY (US); Stephen Royal Kaiser, Chandler, AZ (US); Svein Bergstoel, Sandefjord (NO); Reinhold Bruestle, Zipf (AT); Tunc Icoz, Schenectady, NY (US); Steinar Bjaerum, Horten (NO); Chester Frank Saj, Amsterdam, NY (US)

(73) Assignee: General Electric Company, Niskayuna, NY (US)

( * ) Notice: Subject to any disclaimer, the term of this patent is extended or adjusted under 35 U.S.C. 154(b) by 1516 days.

(21) Appl. No.: 11/639,891

(22) Filed: Dec. 15, 2006

(65) Prior Publication Data

US 2008/0146924 A1    Jun. 19, 2008

(51) Int. Cl.
  *A61B 8/00* (2006.01)
(52) U.S. Cl.
  USPC ........................................................ 600/437
(58) Field of Classification Search
  USPC .................... 600/437, 459; 73/602, 618, 635, 73/636; 310/317, 319
  See application file for complete search history.

(56) References Cited

U.S. PATENT DOCUMENTS

| 4,712,158 A | | 12/1987 | Kikuchi et al. |
|---|---|---|---|
| 5,419,661 A | * | 5/1995 | Meachum .................... 408/57 |
| 5,545,942 A | | 8/1996 | Jaster et al. |
| 5,560,362 A | * | 10/1996 | Sliwa, Jr. et al. ............ 600/439 |
| 5,602,718 A | | 2/1997 | Peszynski |
| 5,721,463 A | * | 2/1998 | Snyder ........................ 310/334 |
| 5,961,465 A | | 10/1999 | Kelly, Jr. et al. |
| 6,666,835 B2 | | 12/2003 | Martin et al. |
| 6,709,392 B1 | | 3/2004 | Salgo et al. |
| 6,766,817 B2 | | 7/2004 | da Silva |

(Continued)

FOREIGN PATENT DOCUMENTS

| EP | 1652476 A2 | 5/2006 |
|---|---|---|
| JP | 05215875 | 8/1993 |

(Continued)

OTHER PUBLICATIONS

"Hydraulics and Pneumatics," "Noise control," pp. 1-4, Feb. 1, 2001 http://www.hydraulicspneu  matics.com/200/FPE/SystemDesign/Article/True/6461/System Design.*

(Continued)

*Primary Examiner* — Tse Chen
*Assistant Examiner* — Patricia Park
(74) *Attorney, Agent, or Firm* — Scott J. Asmus

(57) ABSTRACT

An ultrasound system is provided for imaging an object. The ultrasound system includes an ultrasound probe for acquiring ultrasound data and a cooling subsystem for actively removing heat from the ultrasound probe. The cooling subsystem includes a pump disposed within a reservoir containing a coolant and configured to circulate the coolant through the ultrasound probe via a conduit.

23 Claims, 5 Drawing Sheets

U.S. PATENT DOCUMENTS

| | | |
|---|---|---|
| 6,905,466 B2 | 6/2005 | Salgo et al. |
| 6,918,404 B2 | 7/2005 | da Silva |
| 7,066,586 B2 | 6/2006 | da Silva |
| 2003/0171700 A1 | 9/2003 | Martin et al. |
| 2004/0002655 A1 | 1/2004 | Bolorforosh et al. |
| 2004/0059226 A1 | 3/2004 | Peszynski et al. |
| 2004/0102703 A1 | 5/2004 | Behren et al. |
| 2005/0075573 A1 | 4/2005 | Park et al. |
| 2005/0215892 A1 | 9/2005 | Emery et al. |
| 2005/0215894 A1 | 9/2005 | Dasgupta et al. |
| 2006/0050852 A1* | 3/2006 | Andrews et al. ............... 378/141 |
| 2006/0100513 A1* | 5/2006 | Hashimoto ................... 600/437 |
| 2006/0126884 A1 | 6/2006 | Hielscher |
| 2006/0171505 A1* | 8/2006 | Heidrich et al. .............. 378/123 |
| 2006/0173344 A1 | 8/2006 | Marian et al. |
| 2006/0197780 A1 | 9/2006 | Watkins et al. |

FOREIGN PATENT DOCUMENTS

| | | |
|---|---|---|
| JP | 2001215041 A | 8/2001 |
| JP | 2003038485 A | 2/2003 |
| JP | 2004097402 A | 4/2004 |
| JP | 2004141428 A | 5/2004 |
| JP | 2004321918 A | 11/2004 |
| JP | 2006122198 A | 5/2006 |
| JP | 2006129965 A | 5/2006 |
| JP | 2006204552 A | 8/2006 |
| WO | WO 98/52478 | 11/1998 |
| WO | WO 2005/059586 | 6/2005 |

OTHER PUBLICATIONS

State Intellectual Property Office, P.R. China, Unofficial English Translation of First Office Action issued on Apr. 14, 2010, 14 pages.

* cited by examiner

SYSTEM AND METHOD FOR ACTIVELY COOLING AN ULTRASOUND PROBE

BACKGROUND

The invention relates generally to an ultrasound probe used in ultrasonic imaging of the human anatomy and, more particularly, to a technique for actively cooling the ultrasound probe.

Ultrasound imaging systems have become ubiquitous in the field of medical imaging and diagnostics. Typically, the ultrasound imaging system includes an acoustic probe (ultrasound probe) that is held against a patient. The probe includes acoustic transducers within the probe housing. Each transducer is made of piezoelectric material or electrostatic elements that transmits and receives ultrasound waves, which in turn facilitate the imaging of the internal tissues of the patient. The alternating release and absorption of acoustic energy during transmission and reception creates a thermal build-up in the probe due to acoustic losses being converted into heat.

To obtain the best performance from an ultrasound system it may be desirable to operate the acoustic probe and its associated transducers at a maximum permissible acoustic intensity, such as that allowable by the U.S. Food and Drug Administration. This will enable improvement of the quality of ultrasonic images by increasing the penetration of the acoustic waves so as to maximize the signal to noise ratio for the given system and transducer, and to ensure that imaging performance is not limited by the inability to emit the full allowable acoustic intensity. However, operating the acoustic probe and its associated transducers at higher acoustic intensities may disadvantageously result in the production of excessive heat in the transducer assembly. The amount of heat that can be allowed to build up on the exterior of an ultrasound probe must be within prescribed limits. There exist practical and regulatory limits on the maximum allowable external/surface temperature of an acoustic probe at points of contact with the patient and a technician while performing an imaging procedure. Meeting these goals depends, ultimately, upon the ability to dissipate or extract heat from the probe.

Additionally, the surface temperature of the ultrasound probe must be low enough to avoid harm to the patient and discomfort to the operator. The patient as well as the technician generally prefer to be in contact of a comfortably cool probe during imaging. Further, increased internal temperatures may affect the operational characteristics of the transducer components, thereby reducing their efficiency and/or operating capabilities. For example, CMOS integrated circuits, which may be utilized as part of the control circuitry in the probe, operate faster and more efficiently at lower temperatures.

Moreover, as will be appreciated by one skilled in the art, materials typically employed to fabricate the transducer elements are primarily selected based upon their acoustic properties, and are generally known to possess relatively low intrinsic thermal conductivity. The low thermal conductivity of transducer assemblies may result in the overheating of the probe. Further, most of the heat generated by operation of the probe tends to build up immediately around the transducer elements, which are necessarily situated in the probe very close to the body of the patient being examined. Additionally, the transducer elements are generally isolated from one another by dicing kerfs that provide additional thermal insulation of the transducer elements. Hence, the heat generated within the transducer elements is trapped in the acoustic stack causing the face temperature of the probe to rise above the ambient temperature. It is generally advantageous to dissipate the heat that may be trapped in the array of transducer elements in order to circumvent the overheating of the contact surfaces of the ultrasound probe.

Conventionally, thermal management in ultrasound probes is accomplished with relatively simple devices such as heat conductors, which are buried in the transducer structure so that they transfer heat from the source into the body of the probe structure as quickly as possible. For example, the interior volume of the probe housing surrounding the transducer array may be filled with thermally conductive potting material, e.g., heat-conductive ceramic granules embedded in epoxy. The potting material stabilizes the construction and assists in dissipating heat, generated during pulsation of the transducer element array, away from the probe surface/transducer face toward the interior/rear of the probe. In this way heat is conducted from the critical front surface of the probe into the handle where the increased mass helps dissipate the heat evenly via natural convection.

Because the amount of electronics in conventional ultrasound probes has typically been small enough, natural convection has been sufficient to keep the probe temperature within the regulatory limits. To avoid overheating of the probe, it is common practice to include a thermistor or other temperature sensing device in the probe near the patient contact surface so as to reduce or terminate electrical power and excitations to the probe in the event of overheating.

However, ultrasonic transducer technology is rapidly evolving towards probes with higher element counts. This in turn requires more cabling and lighter-weight materials, and challenges the manufacturability of the interconnect between the individual elements and the ultrasonic imaging system. Added to this strain on the packaging technology is the availability of high levels of circuit integration in semiconductors. Because of the electrical impedance mismatch between the small elements in the transducer and the sensing electronics in the system, various means have been developed to provide active electronics within the probe handle. As electronic technology advances, it is expected that more active circuitry will be placed as near to the source of the detected signal as possible.

The application of semiconductor technology to the diagnostic ultrasonic transducer has created a new dimension in the design and fabrication of these devices. Whereas these products have traditionally been composed of passive electronic circuits and sensors of piezo-electric ceramic, the transducer is now host to active preamplifiers, transmitters, lasers, and ultimately, A/D converters and perhaps digital signal processors. This has significantly increased the requirements for operating power in the probe. This increase in operating power has necessarily led to an increase in operating temperatures. The addition of this technology into the traditionally "hand-held" ultrasonic probe creates severe strains on the ability of the mechanical designer to dispose of the heat generated by the active devices, thereby exacerbating the difficulty of thermal management within the probe. In order to make the highest quality images, the power output of the probe is managed close to the regulatory limit, creating a need to manage the thermal output of the probe.

Thus, with the advent of active devices, the above-described use of heat conductors is no longer sufficient to handle the heat load within the transducer. Ultrasound probes with more electronics in the handle require dissipating higher amounts of heat, such that cooling beyond natural convection is required to meet the regulatory temperature requirements. For example, the heat load dissipated by the simple devices available today is approximately 1 Watt. If preamplifiers are introduced into the system, which dissipate 3 milli Watt in a quiescent mode, the heat load will be increased by 9 Watts for a 3000-element probe, making a total of 10 Watts. Because the current designs are sometimes limited by the temperature of the patient contact area, there is little margin to accommodate this type of thermal output increase. Thus, there is a need to provide thermal transfer mechanisms capable of dissipating greater amounts of heat.

Proposed techniques to enhance the thermal management of the ultrasound probe typically include self-contained cooling systems such as a closed loop circulating cooling system, a thermoelectric cooler, an evaporator/condenser system, channels for circulating cooling liquid about an ultrasonic transducer structure and so forth. These techniques generally have been successful at sufficiently reducing face temperature of the probe. However, this often comes at the expense of the acoustic performance of the transducer assembly. For example, vibrations from pumped cooling fluid may degrade the quality of the image. Similarly, pressure variations during operations may damage the pump/tube. Further, leakage of the cooling fluid from the pump may adversely reduce the life of the cooling systems. Given that it is desirable to be able to operate at the maximum allowable acoustic intensity and also desirable to control the internal transducer operating temperatures as well as the surface temperature distribution of the patient and user-contacting portions of the probe's surfaces, thermal engineering is a serious consideration during transducer design.

It is therefore desirable to provide an efficient and cost effective technique for actively cooling the ultrasound probe so as to facilitate high quality diagnostic imaging by operating the probe at a higher transmit power while maintaining the surface temperature of the probe within regulatory limits. It is also desirable to reduce vibrations, pressure variations and leakage of the cooling fluid from the pump to improve image quality and life of the cooling system.

BRIEF DESCRIPTION

Briefly, in accordance with one aspect of the present technique, an ultrasound system is provided. The ultrasound system includes an ultrasound probe for acquiring ultrasound data, and a cooling subsystem for actively removing heat from the ultrasound probe. The cooling subsystem includes a pump disposed within a reservoir containing a coolant and configured to circulate the coolant through the ultrasound probe via a conduit.

In accordance with another aspect of the present technique, an ultrasound system is provided. The ultrasound system includes an ultrasound probe for acquiring ultrasound data, and a cooling subsystem for actively removing heat from the ultrasound probe. The cooling subsystem includes a pump configured to circulate a coolant through the ultrasound probe via a conduit and a compliant element in a high-pressure portion of the conduit to suppress pressure vibrations.

In accordance with an additional aspect of the present technique, a system is provided for actively cooling an apparatus. The system includes a pump configured to circulate a coolant through the apparatus via a conduit, and a compliant element in a high-pressure portion of the conduit to suppress pressure vibrations.

In accordance with a further aspect of the present technique, a method is provided for actively cooling an apparatus. The method provides for circulating a coolant through the apparatus via a conduit, and suppressing pressure vibrations in a high-pressure portion of the conduit via a compliant element.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present techniques are generally directed to an integrated cooling system for an ultrasound probe. Such an integrated cooling system may be useful in a variety of devices and apparatus that require an efficient and cost-effective thermal management, such as X-ray tubes, electronic devices, electrical and mechanical machines and so forth. Though the present discussion provides examples in context of an ultrasound probe, one of ordinary skill in the art will readily comprehend that the application of these integrated cooling systems in other contexts is well within the scope of the present techniques. It should be noted that the present application makes reference to an imaging "subject" as well as an imaging "object". These terms are not mutually exclusive and, as such, use of the terms is interchangeable and is not intended to limit the scope of the appending claims. Such terms may indicate a human or animal patient, or a device, object or component, such as in manufacturing processes.

Figure 1:
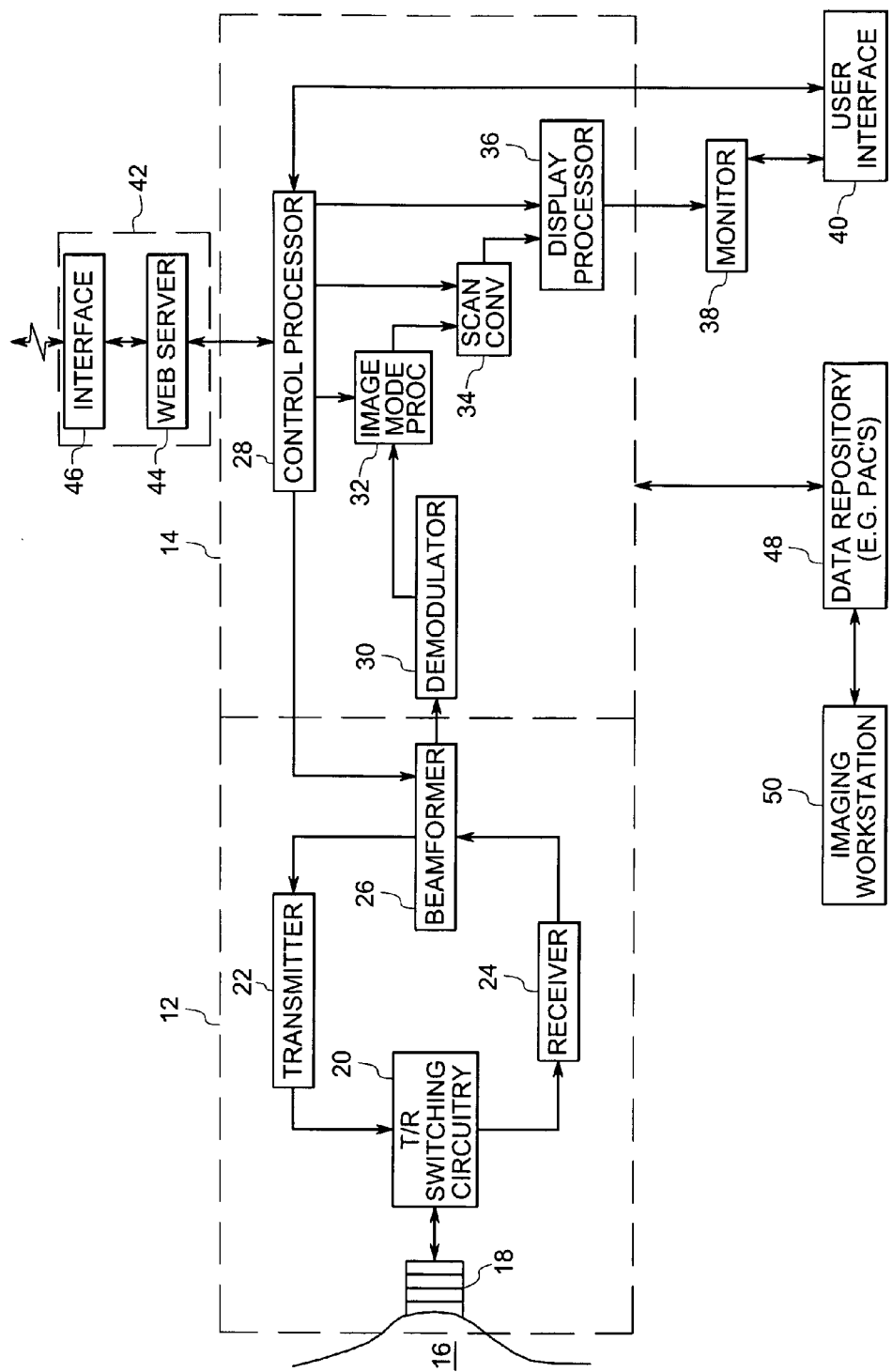
FIG. 1 is a schematic diagram of an exemplary ultrasound system in accordance with aspects of the present technique.

Referring now to FIG. 1, a schematic diagram of an exemplary ultrasound system 10 is illustrated in accordance with aspects of the present technique. The ultrasound system 10 includes an acquisition subsystem 12 and a processing subsystem 14. The acquisition subsystem 12 transmits ultrasound signals into a subject 16 and receives backscattered ultrasound signals from the subject 16. The acquired ultrasound signals are then processed by the processing subsystem 14 to generate an image of the subject 16.

The acquisition subsystem 12 includes a transducer assembly 18, typically an acoustic transducer assembly, which is in contact with a patient or subject 16 during imaging procedure. As will be appreciated by those skilled in the art, the transducer assembly 18 comprises of a plurality of transducer array elements fabricated from materials, such as, but not limited to lead zirconate titanate (PZT), polyvinylidene difluoride (PVDF) and composite PZT. It should be noted that the transducer assembly 18 is a two-way transducer and is configured to transmit ultrasound waves into and receive such energy from the subject 16. In transmission mode, the transducer array elements convert the electrical energy into ultrasound waves and transmit it into the subject 16. In reception mode, the transducer array elements convert the ultrasound energy received from the subject (backscattered waves) into electrical signals.

The acquisition subsystem 12 further includes transmit/receive switching circuitry 20, a transmitter 22, a receiver 24, and a beamformer 26. The transmit/receive (T/R) switching circuitry 20 is coupled to the transducer array 18 for switching the transducer array 18 into transmission or reception mode. To generate ultrasound waves for transmission into the subject 16, the processing subsystem 14 sends transmit command data to the beamformer 26. On receiving the transmit command data, the beamformer 26 generates transmit parameters to create a beam of a desired shape originating from a certain point at the surface of the transducer array 18 at a desired steering angle. The beamformer 26 then sends the transmit parameters to the transmitter 22. The transmitter 22 uses the transmit parameters to properly encode transmit signals to be sent to the transducer array 18 through the T/R switching circuitry 20. The transmit signals are set at certain levels and phases with respect to each other and are provided to individual transducer elements of the transducer assembly 18. The transmit signals excite the transducer elements to emit ultrasound waves with the same phase and level relationships. As a result, a beam of ultrasound energy is formed in a subject 16 within a scan plane along a scan line when the transducer assembly 18 is acoustically coupled to the subject 16 by using, for example, ultrasound gel. The process is known as electronic scanning.

The transmitted ultrasound waves are then backscattered off the tissue and blood samples within the subject 16. The transducer array elements receive the backscattered waves at different times depending on the distance into the tissue they return from and the angle with respect to the surface of the transducer assembly 18 at which they return. As stated above, the transducer array elements receive the backscattered ultrasound signals from the subject 16 and convert it into electrical signals. The electrical signals are then routed through the T/R switching circuitry 20 to the receiver 24. The receiver 24 amplifies and digitizes the received signals and provides other functions such as gain compensation. The digitized received signals corresponding to the backscattered ultrasound waves received by each transducer element at various times preserve the amplitude and phase information of the backscattered waves. The digitized signals are then sent to the processing subsystem 14 through beamformer 26. The processing subsystem 14 sends receive command data to beamformer 26. The beamformer 26 uses the receive command data to form a receive beam originating from a point on the surface of the transducer assembly 18 at a steering angle typically corresponding to the point and steering angle of the previous ultrasound beam transmitted along a scan line. The beamformer 26 operates on the appropriate received signals by performing time delaying and focusing, according to the instructions of the command data from the control processor 28, to create received beam signals corresponding to sample volumes along a scan line in the scan plane within the subject 16. The phase, amplitude, and timing information of the received signals from the various transducer elements is used to create the received beam signals.

The processing subsystem 14 includes a control processor 28, a demodulator 30, an imaging mode processor 32, a scan converter 34 and a display processor 36. The control processor 28 interfaces with the imaging mode processor 32, the scan converter 34 and the display processor 36. Additionally the control processor is responsible for sending transmit and receive command data to the beamformer 26. The demodulator 30 demodulates the received beam signals to create pairs of I and Q demodulated data values corresponding to sample volumes within the scan plane. Demodulation is accomplished by comparing the phase and amplitude of the received beam signals to a reference frequency. The I and Q demodulated data values preserve the phase and amplitude information of the received signals.

The demodulated data is transferred to the imaging mode processor 32. The imaging mode processor 32 uses parameter estimation techniques to generate imaging parameter values from the demodulated data in scan sequence format. The imaging parameters may include parameters corresponding to various possible imaging modes such as B-mode, color velocity mode, spectral Doppler mode, and tissue velocity imaging mode, for example. The imaging parameter values are passed to the scan converter 34. The scan converter 34 processes the parameter data by performing a translation from scan sequence format to display format. The translation includes performing interpolation operations on the parameter data to create display pixel data in the display format.

The scan converted pixel data is sent to the display processor 36 to perform any final spatial or temporal filtering of the scan converted pixel data, to apply grayscale or color to the scan converted pixel data, and to convert the digital pixel data to analog data for display on the monitor 38. The user interface 40 is coupled to the control processor 28 to allow a user to interface with the ultrasound system 10 based on the data displayed on the monitor 38.

The display processor 36 is further coupled to a display monitor 38 for displaying images. User interface 40 interacts with the control processor 28 and the display monitor 38. The control processor 28 may also be coupled to a remote connectivity subsystem 42 including a web server 44 and a remote connectivity interface 46. The processing subsystem 14 may be further coupled to a data repository 48 configured to receive ultrasound image data. The data repository 48 interacts with image workstation 50.

The aforementioned components may be dedicated hardware elements such as circuit boards with digital signal processors or may be software running on a general-purpose computer or processor such as a commercial, off-the-shelf personal computer, or specialized workstation. The various components may be combined or separated according to various embodiments of the invention. Thus, those skilled in the art will appreciate that the ultrasound system 10 described above is provided by way of example, and the present techniques are in no way limited by the specific system configuration.

As will be appreciated by one skilled in the art, most of the components of the acquisition subsystem 12 and some of the components of processing subsystem 14 may be housed within a portable ultrasound probe. Additionally, a cooling subsystem may be disposed within the ultrasound probe for actively removing heat from the ultrasound probe in accordance with aspects of the present technique.

Figure 2:
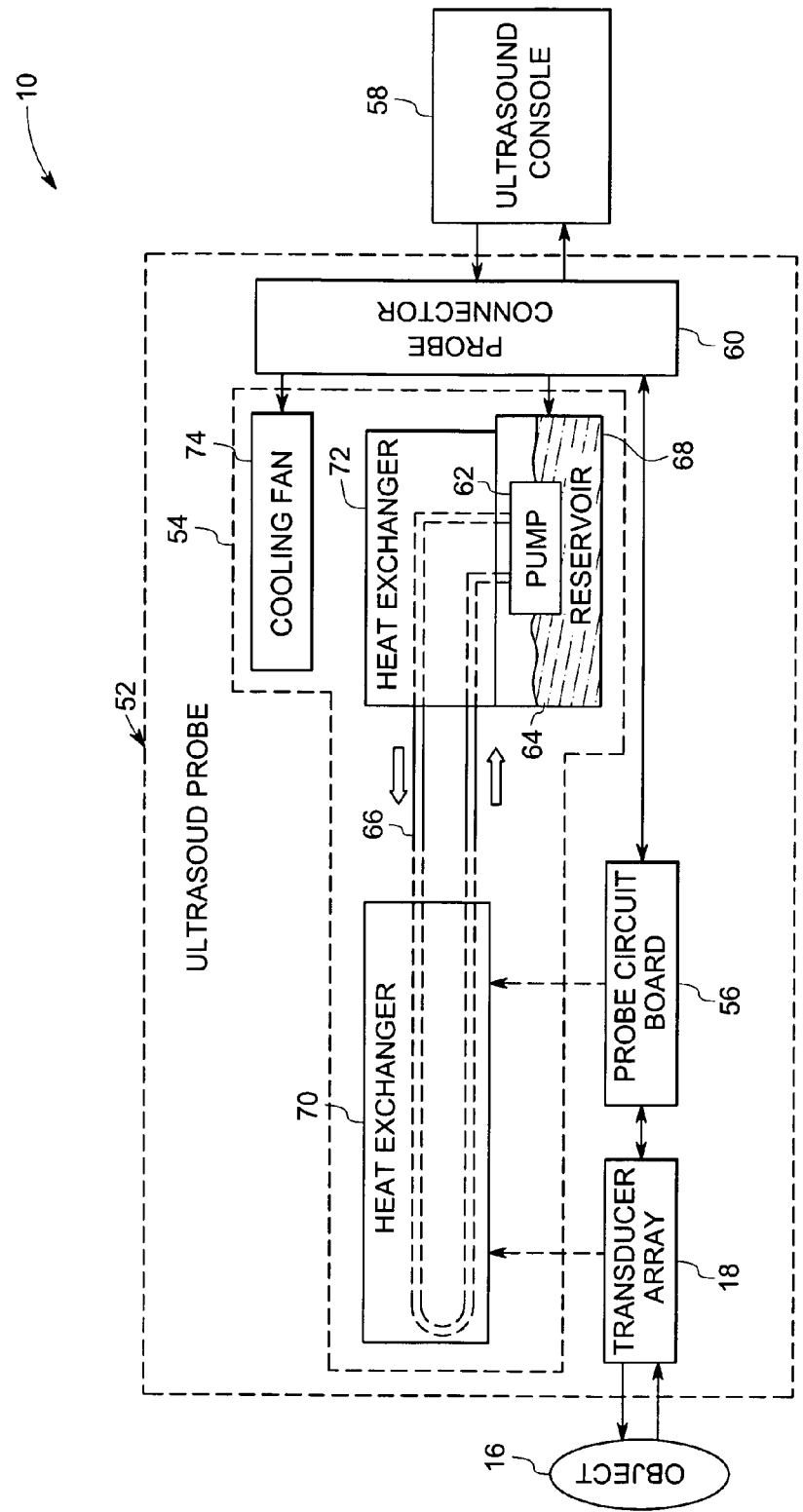
FIG. 2 is a schematic diagram of an ultrasound probe illustrating a self contained cooling system in accordance with aspects of the present technique.

FIG. 2 illustrates a schematic diagram of an ultrasound probe 52 employing a self-contained cooling subsystem 54 in accordance with aspects of the present technique. As illustrated, the ultrasound probe 52 includes the transducer assembly 18 and associated electronics for acquiring ultrasound data by transmitting ultrasound signals to and receiving signals from the subject 16. The associated electronics may be mounted on a probe circuit board 56. The ultrasound probe 52 is controlled by an ultrasound console 58, which furnishes power, acquisition parameters, control signals and so forth for imaging sequences. The ultrasound console 58 is typically coupled to the ultrasound probe 52, and in particular to the probe circuit board 56, via a probe connector 60 and may include a microprocessor, digital signal processor, microcontroller, as well as other devices designed to carry out control and processing operations. Additionally, the ultrasound console 58 furnishes power to the cooling subsystem 54 via the probe connector 60. Furthermore, the ultrasound console 58 may be configured to receive commands and scanning parameters from an operator via a keyboard and/or other input devices. An operator may thereby control the ultrasound system 10 via the ultrasound console 58. Thus, the operator may observe the ultrasound image and other data relevant to the system, initiate imaging, and so forth.

The cooling subsystem 54 is housed within the ultrasound probe 52 and includes a pump 62 configured to circulate a coolant 64 through the ultrasound probe 52 (between the probe unit, probe handle and the probe connector) via a conduit 66. In certain embodiments, the pump 58 may be placed within a reservoir 68 containing the coolant 64. It should be noted that the reservoir 68 may be partially or completely filled with the coolant 64 and the pump 62 may be submerged or partially submerged within the coolant 64. Alternatively, the pump 62 may be within the reservoir 68 but still not submerged within the coolant 64. Typically, certain pumps 62 may be constructed with a compliant diaphragm that tends to leak significantly while pumping the coolant, thereby requiring unreasonably large amounts of coolant over a product life. As will be appreciated by one skilled in the art, placing the pump within the reservoir minimizes the need to replace coolant during the product life, thereby making the cooling subsystem highly reliable. Any leakage from the diaphragm is simply recycled to the reservoir and is not lost from the cooling system. In addition the cooling fluid provides good thermal transfer between the pump and reservoir, thereby allowing for more efficient cooling of the pump. Additionally, various means to reduce coolant loss at joints may be employed. For example, the conduit may be fastened or secured at various joints though fasteners. These fasteners may include, but are not limited to, heat shrink tubing, O-rings, and metal ferrules. In certain embodiments, non-leaking pumps such as peristaltic pump may be employed to circulate the coolant 64 through the ultrasound probe 52.

As will be appreciated by one skilled in the art, in certain embodiments, a fluid level sensor (not shown) may be employed to monitor or measure the coolant level within the reservoir for indicating the requirement of additional coolant when the coolant level falls below a certain predetermined level. The coolant level can be determined either directly by measuring capacitance gauge, or by using part of the imager's Doppler signal processor. A replenishment means may be provided to allow replenishment of the coolant in order to compensate for the coolant loss. In one embodiment, the replenishment means may include a silicone or basketball valve like orifice into reservoir that replenishes the coolant by permeation. Additionally, a silicone damping material may be provided between the pump motor and the reservoir to reduce acoustic noise.

The cooling subsystem 54 further includes a first heat exchanger 70 thermally coupled to the ultrasound probe 52 for removing heat from the ultrasound probe 52. In particular, the first heat exchanger 70 is thermally coupled to the transducer assembly 18 and the probe circuit board 56 through the heat spreaders for removing heat from these components as most of the heat may be generated in these components. Additionally, the conduit 66 carrying the coolant 64 is thermally coupled to the first heat exchanger 70 for removing heat from the first heat exchanger 70. The coolant 64 flows via the conduit 66 through the first heat exchanger 70 and is heated by the first heat exchanger 64 during the flow, which in turn was heated by the transducer assembly 18 and the probe circuit board 56. The heated coolant 64 is circulated through the conduit 66 to a second heat exchanger 72 thermally coupled to the conduit 66 where the heat is conveyed to ambient air through a combination of conduction and convection. The conduit 66 therefore forms a closed loop path between the first heat exchanger 70, the second heat exchanger 72, and the pump 62 and the coolant is circulated through this closed loop path. A cooling fan 74 may be placed near the second heat exchanger 72 for cooling the second heat exchanger 72.

As will be appreciated by one skilled in the art, the first and the second heat exchangers 70 and 72 may be made of flat copper sheets. Further, it should be noted that the first and the second heat exchanger may be a multi-part heat exchangers. Each part may then be placed on different sides of the heat source to reduce the thermal resistance between the source and the respective heat exchanger. Additionally, as will be appreciated by one skilled in the art, the cross flow reservoir/heat exchanger may be designed to maximize cooling efficiency and cooling fluid volume. The heat spreaders may be any thermally conductive material such as aluminum, copper, graphite, thermally annealed pyrolytic graphite (TPG) and so forth. A thermal interface material may be provided for enhanced thermal transport from the electronics to the first heat exchanger. The thermal interface material may be any thermally conductive interface material such as silicone pads, greases, graphite pads and so forth. In certain embodiments, the coolant 64 may be a dielectric liquid such as flourocarbon. Further, in certain embodiments, the conduit 66 may be a thin plastic tube made of flouro-ethylene propylene (FEP).

As stated above, the pumped coolant 64 may cause pressure vibrations in the ultrasound probe 52 during operation, which in turn can degrade the quality of the image or damage the pump or tube. The pump pushes small amounts of fluid in a pulsatile fashion, similar to a piston pump. The pulsatile flow may create vibration in the outflow tube unless some form of volume compensation is provided between the pump outflow and the tubing. Because the probe is non-mechanical, any vibration may be undesirable, and thus it may be desirable to minimize vibrations. Moreover, the vibration may be coupled to the transducer and cause artifacts in the ultrasound image. It should be noted that a similar effect could also occur at the intake when the pump pulls in fluid. A vapor buffered expansion chamber from which the pump draws the fluid may be incorporated to reduce these vibrations. An expansion unit near the pump outflow greatly reduces the vibration in the downstream tubing.

Figure 3:
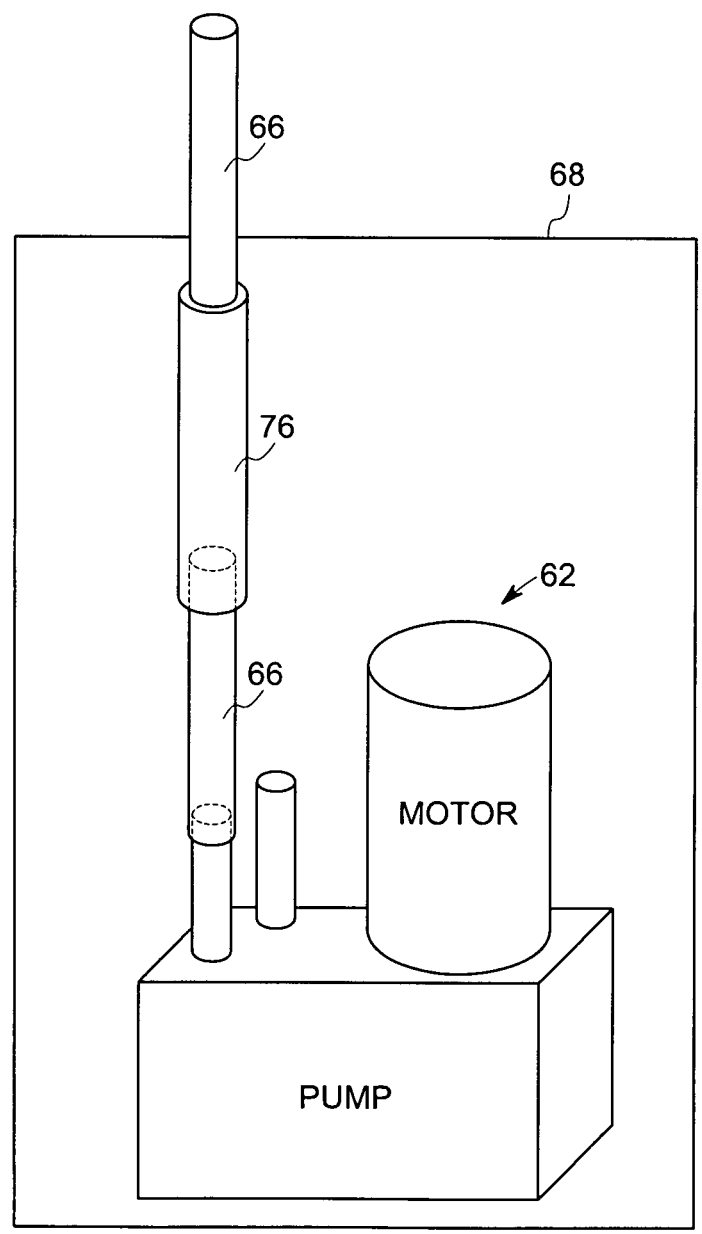
FIG. 3 is a schematic diagram illustrating a mechanism for suppressing pressure vibrations within a conduit of the cooling system in accordance with one aspect of the present technique.
Figure 4:
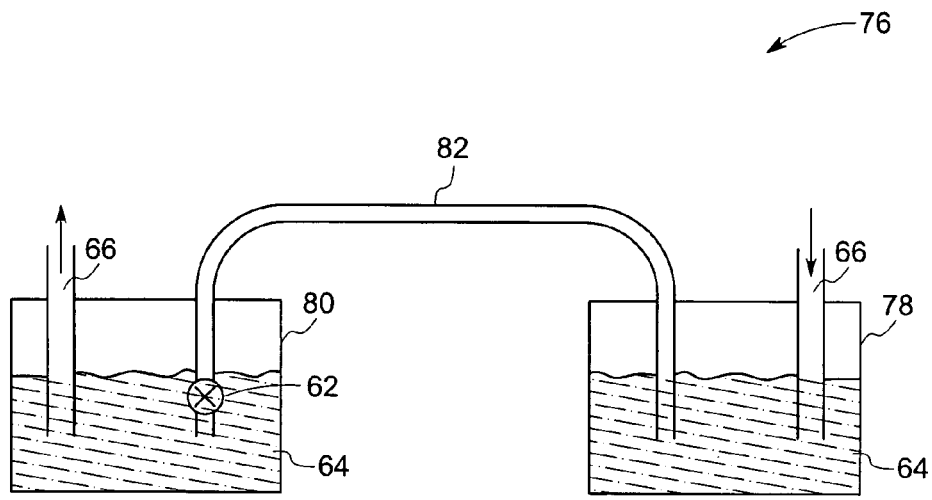
FIG. 4 is a schematic diagram illustrating a mechanism for suppressing pressure vibrations within the conduit of the cooling system in accordance with another aspect of the present technique.
Figure 5:
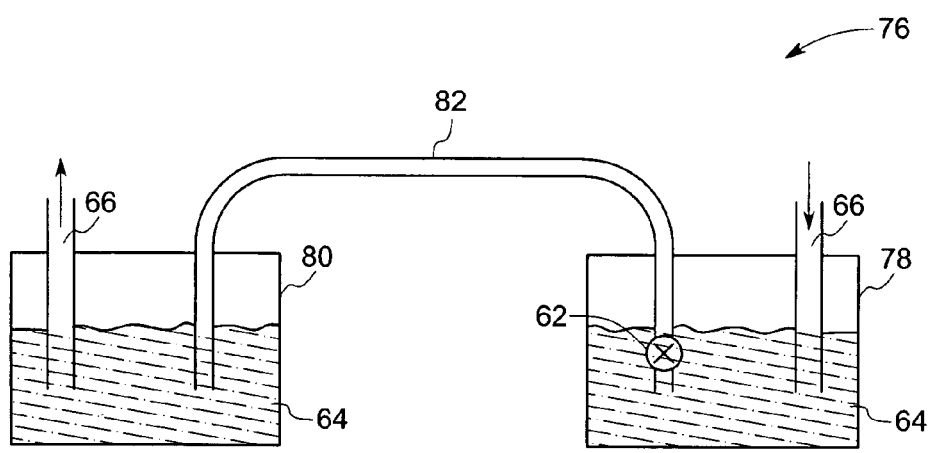
FIG. 5 is a schematic diagram illustrating a mechanism for suppressing pressure vibrations within the conduit of the cooling system in accordance with a further aspect of the present technique.

FIGS. 3-5 illustrate various mechanisms for suppressing pressure vibrations within the conduit 66 of the cooling system 54 in accordance with aspects of the present technique. As illustrated, a compliant element 76 may be employed in high-pressure portions of the conduit 66 to suppress pressure vibrations. For example, in certain embodiments, the compliant element 76 may be a compliant tube (expansion tube) placed near the outlet of the pump 62 within the reservoir 68 to suppress pulsatile vibrations caused by pulsatile pumping as illustrated in FIG. 3. It should be noted that the compliant tube may be incorporated into the fluid reservoir to avoid the coolant loss as any permeation through this section will simply return coolant to the reservoir. A silicone tube of appropriate diameter and length dampens the pressure variations and thereby reduces image artifacts. Additionally, a metal braid, a piece of solder wick, or a piece of larger-diameter less compliant/non-compliant tubing may be disposed over the compliant tube to prevent it from expanding too much. It should be noted that when the tube begins to expand, there is very little resistance to the motion. The metal braid, the piece of solder wick, or the piece of larger-diameter less compliant/non-compliant tubing helps in moving the expansion to another part of the tube rather than causing a positive feedback condition to further expand the tube.

Alternatively, in certain embodiments, the compliant element 76 may include a two reservoirs system to suppress the pressure vibrations. As illustrated in FIG. 4 and FIG. 5, the two reservoirs system may include an inlet reservoir 78 for receiving incoming conduit 66 and an outlet reservoir 80 from which the outgoing conduit originates. Both the reservoirs 78 and 80 are partially filled with the coolant 64 and are connected to each other via the pump 62 and the conduit 82. As will be appreciated by one skilled in the art, the compliant element 76 may include other arrangements to suppress the pressure vibrations. For example, in certain embodiments, the boundary between the coolant 64 and air/vapor within the reservoir 68 partially filled with the coolant 64 or between the coolant 64 and outside environment may act as the compliant element 76. Similarly, in certain embodiments, a compliant structure, such as a membrane or a bellows, between the coolant 64 and air/vapor within the reservoir 68 partially filled with the coolant 64 or between the coolant 64 and the outside environment may act as the compliant element 76.

As will be appreciated by those skilled in the art, it is not uncommon for ultrasound operators to roll the console over the cable connecting the probe handle to the console, thereby potentially damaging the cable conducting signals to and from the probe and the tubes carrying the coolant. In particular, the conduit 66 may be blocked in such cases, thereby forcing the pump 62 to work against an elevated pressure and making it susceptible to damage. A variety of techniques may be employed to release excess pressure built up within the conduit 66 of the cooling system 54 in accordance with aspects of the present technique. Such pressure limiting technique is typically based on providing a bypass pathway for the coolant 64 to release excess pressure built up within the conduit 66 when the conduit 66 is blocked. As will be appreciated by one skilled in the art, the bypass pathway is activated if the conduit pressure rises above a threshold pressure. In one embodiment, the threshold pressure is equal to twice the atmospheric pressure and the bypass pathway prevents the pump from pumping against a pressure greater than the threshold pressure. Further, it should be noted that the bypass pathway may be provided within the reservoir or constructed as part of the reservoir such that the coolant 64 flows back into the reservoir 68.

If, under normal operation, a coolant flow of $I_1$ through a loop of resistance $R_1$ is desired and to avoid damage a minimum flow $I_{min}$ at maximum pressure $V_{max}$ needs to be maintained, then the shunt (bypass pathway) should have resistance $R_2 = V_{max}/I_{min}$ and the cooling system's normal operating point should be pressure $V = I_1 R_1$ and the coolant flow $I = I_1, (1+R_1/R_2)$.

Figure 6:
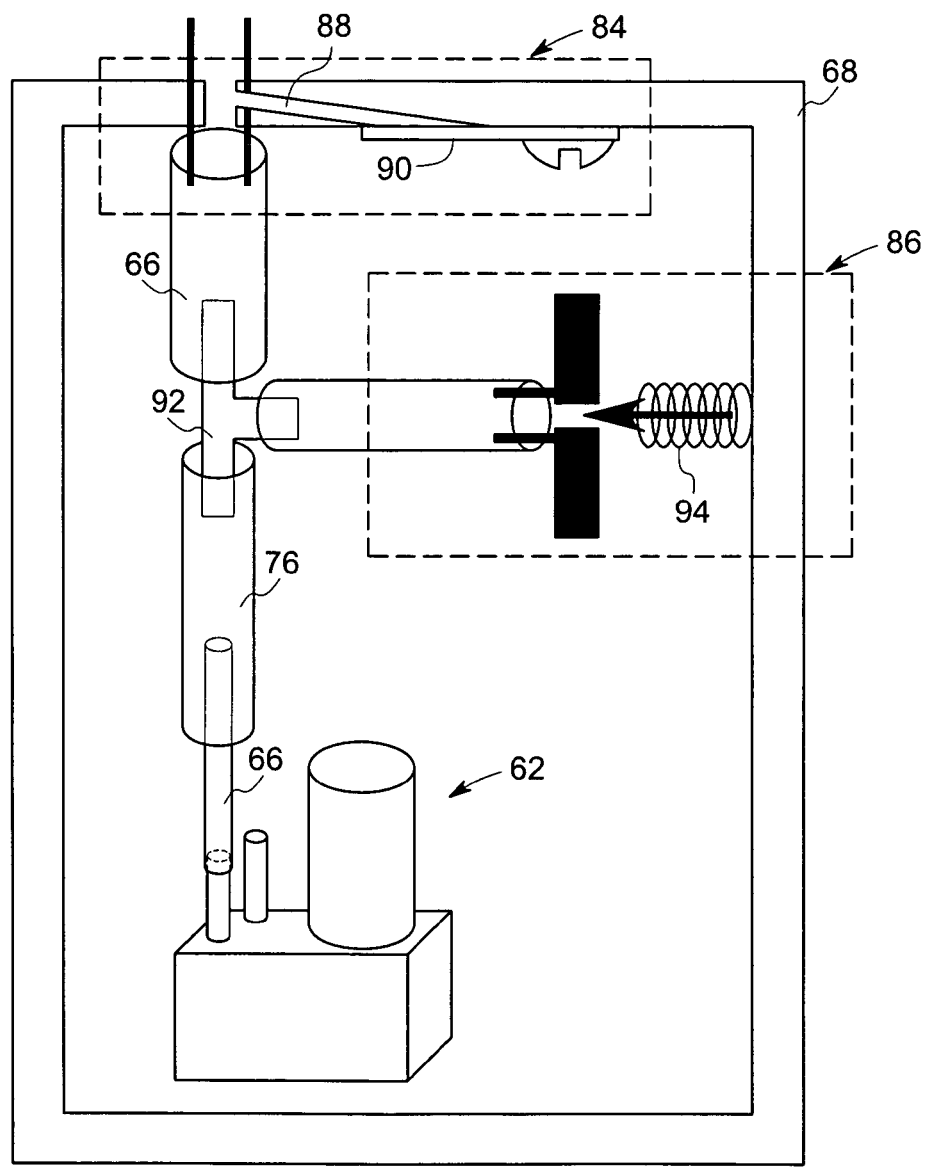
FIG. 6 is a schematic diagram illustrating various mechanisms for releasing excess pressure built up within the conduit of the cooling system in accordance with aspects of the present technique.

FIG. 6 illustrates two such techniques (overpressure relief systems 84 and 86) for releasing excess pressure built up within the conduit 66. As illustrated, the overpressure relief system 84 includes a bypass pathway 88 and a spring shim 90. Under normal conditions, the spring shim 90 blocks the bypass pathway 88. When the pressure within the conduit 66 rises above the threshold pressure, the coolant 64 exerts pressure on the spring shim 90. The spring shim 90 bends under the pressure, thereby allowing the coolant a path to flow back into the reservoir 68. Similarly, as illustrated, the overpressure relief system 86 includes a bypass pathway 92 and a spring needle valve 94. Under normal conditions, the spring needle valve 94 blocks the bypass pathway 92. When the pressure within the conduit 66 rises above the threshold pressure, the coolant 64 exerts pressure on the spring needle valve 94. The spring needle valve 94 is pushed back under the pressure, thereby allowing the coolant a path to flow back into the reservoir 68. As will be appreciated by one skilled in the art, in certain embodiments, a bellows or a piston (not shown) may be coupled to the spring needle valve 94 such that the excess pressure acts on the bellows or the piston of well-defined area and not on the spring needle valve 94. This arrangement will provide a better control of pressure at which the valve opens, particularly if the valve has or acquires some throttling ability (resistance to flow gradually decreases over time as valve is opens and closes). It should be noted that, in certain embodiments, the overpressure relief systems 84 and 86 may be provided after the compliant element 76 for vibration suppression.

As will be appreciated by one skilled in the art, the cooling subsystem 54 described in the various embodiment discussed above has improved efficiency, compactness and robustness. The cooling subsystem 54 remains self-contained in the ultrasound probe 52. Apart from electricity to run various components, no other services are needed from the console. This makes it comparatively easy to use such a probe with many pre-existing consoles. The self-contained cooling subsystem, utilizes an encapsulated pump to minimize leaks, thereby reducing or eliminating the need for fluid replacement during the service life. The techniques, described in various embodiments discussed above, reduce or eliminate vibrations from pulsatile flow of pumped cooling fluid that can degrade image quality, thereby reducing or eliminating image artifacts caused by pulsating fluid. Additionally, the techniques, described in various embodiments discussed above, protect the pump from damage in the event of operator errors that leads to overpressure due to blockages in the conduit. Moreover, as will be appreciated by one skilled in the art, the conventional safety feature for preventing over heating such as switching off power, reducing power supply, decreasing acoustic intensity and so forth may be retained to provide additional safety to the ultrasound probe.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An ultrasound system, comprising:
 a portable ultrasound probe for contacting a subject and acquiring ultrasound data, comprising:
 a self-contained cooling subsystem disposed in said portable ultrasound probe configured to actively removing heat from the ultrasound probe, the self-contained cooling subsystem comprising a pump configured to circulate a coolant through the ultrasound probe via a conduit, the pump being disposed within a reservoir containing the coolant; and a compliant element in a high-pressure portion of the conduit configured to suppress pressure vibrations, wherein the self-contained cooling subsystem is disposed within the portable ultrasound probe.

2. The ultrasound system of claim 1, wherein the cooling subsystem further comprises a first heat exchanger thermally coupled to the ultrasound probe and the conduit configured to remove heat from the ultrasound probe.

3. The ultrasound system of claim 1, wherein the cooling subsystem further comprises a second heat exchanger thermally coupled to the conduit configured to remove heat from the coolant.

4. The ultrasound system of claim 3, wherein the cooling subsystem further comprises a cooling fan configured to cool the second heat exchanger.

5. The ultrasound system of claim 1, wherein the coolant is a dielectric liquid.

6. The ultrasound system of claim 1, wherein the conduit comprises a plastic tube.

7. The ultrasound system of claim 1, wherein the coolant is circulated in a closed loop path.

8. The ultrasound system of claim 1, wherein the conduit is fastened at one or more joints via fasteners configured to reduce coolant loss at the one or more joints.

9. The ultrasound system of claim 1, wherein the cooling subsystem further comprises a fluid level sensor configured to monitor coolant level within the reservoir.

10. The ultrasound system of claim 1, wherein the cooling subsystem further comprises an orifice into the reservoir configured to replenish the coolant within the reservoir.

11. The ultrasound system of claim 1, wherein the cooling subsystem further comprises a damping material between the pump and the reservoir configured to reduce acoustic noise.

12. The ultrasound system of claim 1, wherein the compliant element comprises a boundary between the coolant and air or vapor within the reservoir partially filled with the coolant.

13. The ultrasound system of claim 1, wherein the compliant element comprises a membrane or a bellows between the coolant and air or vapor within the reservoir partially filled with the coolant or between the coolant and outside environment.

14. The ultrasound system of claim 1, wherein the compliant element comprises a compliant tube placed near the pump outlet within the reservoir.

15. The ultrasound system of claim 14, further comprising a metal braid, a piece of solder wick, or a piece of larger-diameter less compliant/non-compliant tubing disposed over the compliant tube configured to reduce over-expansion of the compliant tube.

16. An ultrasound system, comprising:
    a portable ultrasound probe configured to contact a subject and acquiring ultrasound data; and
    a self-contained cooling subsystem configured to actively remove heat from the ultrasound probe, the self-contained cooling subsystem comprising:
        a pump configured to circulate a coolant through the ultrasound probe via a conduit, wherein the pump is disposed within a reservoir containing the coolant; and
        a compliant element in a high-pressure portion of the conduit configured to suppress pressure vibrations, wherein the self-contained cooling subsystem is disposed within the ultrasound probe.

17. A self-contained system configured to actively cool a portable ultrasound probe, the self-contained system comprising:
    a pump configured to circulate a coolant through the portable ultrasound probe via a conduit, wherein the pump is disposed within a reservoir containing the coolant; and
    a compliant element in a high-pressure portion of the conduit configured to suppress pressure vibrations, wherein the self-contained system is disposed within the portable ultrasound probe.

18. The system of claim 17, further comprising a first heat exchanger thermally coupled to the apparatus and the conduit configured to remove heat from the apparatus.

19. The system of claim 17, further comprising a second heat exchanger thermally coupled to the conduit configured to remove heat from the coolant.

20. A method for actively cooling a portable ultrasound probe, the method comprising:
    circulating a coolant through the portable ultrasound probe via a conduit by a pump, wherein the pump is disposed within a reservoir containing the coolant;
    suppressing pressure vibrations in a high-pressure portion of the conduit via a compliant element; and
    cooling the ultrasound probe from within using a self-contained cooling subsystem disposed in the portable ultrasound probe.

21. The method of claim 20, further comprising removing heat from the ultrasound probe via a first heat exchanger thermally coupled to the ultrasound probe and the conduit.

22. The method of claim 20, further comprising removing heat from the coolant via a second heat exchanger thermally coupled to the conduit.

23. The method of claim 22, further comprising cooling the second heat exchanger via a cooling fan.

* * * * *